US00PP20461P2

(12) United States Plant Patent

Deng et al.

(10) Patent No.: US PP20,461 P2

(45) Date of Patent: Nov. 10, 2009

(54) *CALADIUM* PLANT NAMED 'FIRECRACKER RED'

(50) Latin Name: *Caladium×hortulanum*
Varietal Denomination: Firecracker Red

(75) Inventors: Zhanao Deng, Wimauma, FL (US); Brent Harbaugh, Wimauma, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/151,718

(22) Filed: May 9, 2008

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

OTHER PUBLICATIONS

Deng Ziaanao et al. Proceedings of the 119th Annual meeting of the Florida State Horticultural Society. Proceedings of the Florida State Horticultural Society 119 p. 409-412. 2006. abstract.*

* cited by examiner

*Primary Examiner*—Annette H Para

(57) ABSTRACT

A distinct cultivar of *Caladium* plant named 'Firecracker Red', characterized by its very large heart shaped leaves, bright red color, and demonstrated potential to produce large plants with huge leaves when grown in outdoor landscapes.

1 Drawing Sheet

BACKGROUND OF THE INVENTION

'Firecracker Red' was a seedling initially evaluated in 2001 as GC274 originating from the cross-pollination of the *Caladium×hortulanum* cultivar Red Frill with the cultivar White Queen made in a greenhouse in Bradenton, Fla. 'Red Frill', not patented, was selected as the female (seed parent) parent because of its multi-branching characteristics and bright red leaf color. 'White Queen', not patented, was the male (pollen) parent selected because of its large leaves and bright red vein color. Ancestry of 'Red Frill' and 'White Queen' are unknown. Asexual propagation by tuber division was done in Bradenton, Fla. and Dover, Fla. Evaluation in field and pot studies since 2001 have shown that the unique features of this new *Caladium* plant are stable and reproduced true to type in successive generations of asexual propagation.

SUMMARY OF THE INVENTION

The new *Caladium* has not been observed under all possible environmental conditions. The phenotype may vary somewhat with variations in the environment such as light intensity and temperature, without, however, any variance in genotype.

*Caladiums* are utilized in the ornamental industry as potted plants and landscape plants. They have a diversity of leaf colors that arise from red, pink, and white pigments displayed in solid, spot, and/or blotch patterns in interveinal areas. Veins and leaf margins may be colored or green adding to the diversity of patterns. For plants to be successful in the landscape, they must be vigorous, brightly colored, and have large leaves (unless used for border plants such as is the case for strap or lance leaved cultivars). When forced in containers to be used as an ornamental potted plant, shorter plants with many leaves that emerge quickly are desirable traits. The new *Caladium* plant, 'Firecracker Red', has a distinct bright red center (venation and interveinal areas) with a dark green border on very large heart shaped leaves. Its large leaves make it very different from 'Red Frill', the female parent, which has narrow (strap leaved) leaves. It is different in color from 'White Queen', the male parent, which has white leaves with red primary veins. It is taller than both parents when planted in the landscape. 'Firecracker Red' has performed well in landscape settings in a number of trials showing the height, leaf size, and vigor necessary for landscape use. Tuber production, a necessary consideration for commercialization of a cultivar by the *Caladium* tuber producing industry, has been excellent with tubers produced in the ideal sizes as described in the description section.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description, which accurately describe the colors of the new *Caladium*.

The photograph, labeled FIG. 1, illustrates the overall appearance of the new cultivar, Firecracker Red. The photograph is a side perspective view of a typical plant of 'Firecracker Red' grown in a container.

DETAILED BOTANICAL DESCRIPTION

The following is a detailed description of the new variety with color terminology in accordance with British Color Council and The Royal Horticultural Society, Horticultural Colour Chart, except where general color terns of ordinary dictionary significance are obvious. Wherein dimensions, sizes, and other characteristics are given, it is to be understood that such characteristics are approximations of averages set forth as accurately as practicable. The description herein is from 4 month old specimens grown in Bradenton, Fla., in 2003–2005. Plants used for describing color were grown in 15 cm containers in a 40% shaded greenhouse from Jumbo (6.4 to 8.9 cm diameter) de-eyed tubers.

Botanical classification: *Caladium×hortulanum* cultivar Firecracker Red.

Propagation:

*Type.*—By tuber division.

*Time to develop roots and sprout.*—41 days (Spring — 15° C. night to 29° C. day). 17 days (Summer — 21° C. night to 35° C. day).

Root description.—Dense, thick roots (up to 2.8 mm at the basal end) with little branching and few lateral roots.

Plant description:

*Plant shape.*—Upright, symmetrical.

*Plant height.*—About 56 cm from top of soil to top of leaf plane 4 months from planting tubers in ground beds in full sun.

*Leaf blade.*—Leaves are peltate, sagitate-cordate, 29–33 cm long and 20–22 cm wide, with red (RHS 46A) palmate-pinnate venation. The upper surface has a green (RHS 147A) irregular margin, 2–4 cm wide, bordering the entire leaf except for the basal leaf valley where it is grayed-purple (RHS 185A). Interveinal areas are red (RHS 46A) diffusing into a grayed-purple (RHS 185A) toward the leaf margin. The undersurface is primarily grayed-green (RHS 191A) grayed-green (RHS 191A) with primary veins and a small interveinal area around these veins prayed purple (RHS 186A).

*Petiole.*—Petioles are 4–5 mm in diameter and streaked dark red-purple (RHS 71A) and light red-purple (RHS 73D).

*Tuber.*—Tubers are multi-segmented; a tuber 6.4–8.9 cm in diameter will typically bear 3 dominant buds. Tuber surfaces are brown (RHS 200A–B) with the cortical area yellow (RHS 4C) to a darker yellow-orange (RHS 8B).

*Inflorescence.*—The flowering and reproductive organs do not differ in character from other *Caladium* plants.

Performance:

*Firecracker Red*=was evaluated for tuber production and plant performance at the Gulf Coast REC—Bradenton, Fla. during 2003 and at Dover, Fla. in 2004. The soil was an EauGallie fine sand with about 1% organic matter and a pH of 6.2. Plants were grown in a plastic-mulched raised-bed system maintaining a constant water table with seep irrigation. The beds were 91 cm wide and 20 cm high with 2.54 cm *Caladium* seed pieces planted 15 cm apart in 3 rows (Bradenton) or 2 rows (Dover) also spaced 15 cm apart. Osmocote 18N-2.6P-10K 8–9 month controlled release fertilizer was applied to the bed surface when shoot tips were emerging from the soil with N at 336 kgXha$^{-1}$ .

Plots were organized in a randomized complete block design consisting of three replications. For tuber production, each plot was 1.2 m$^2$ and contained 30 propagules. An analysis of variance was conducted in order to compare the performance of >Firecracker Red= to its parents and other important other commercially important white fancy-leaf cultivars. For plant performance in the landscape, three plants were measured in the center of each plot and plant height, leaf number, and leaf size were measured mid-summer. Since year did not significantly influence plant performance, the data was averaged over the 2 years.

'Firecracker Red' tuber production was excellent with tuber weights nearly 1.5 times higher than 'Frieda Hemple' and 'Postman Joyner', the two most popular red-leaved fancy cultivars. 'Firecracker Red' tuber weight from each plot exceeded all cultivars except 'Florida Cardinal' in 2004 (Table 3) when yields were similar. Similarly, the production index (an economic indicator of crop value) was highest for 'Firecracker Red' compared to all other cultivars except 'Florida Cardinal' that had similar high values. Although the same number (30) of seed pieces were planted per plot, more than 30 tubers were harvested since several sprouts may emerge per tuber and result in more than one tuber developing per planted seed piece. This of course is advantageous as it can increase profitability. Although 'Firecracker Red' did not have the greatest number of marketable tubers, it ranked high compared to many other cultivars. Since it forms a "solid" tuber with few side tubers, it does not break apart into many small tubers during harvest that is a problem with some cultivars like 'Frieda Hemple'. The lack of breakage for 'Firecracker Red' is also evident in the high percentage of Mammoth, Jumbo and No. 1 tubers (95% in 2003 and 84% in 2004), ideal sizes for tubers sold for use in the landscape.

Landscape performance of cultivars grown under full-sun conditions was evaluated in 2003 and 2004 on the same plots used for evaluating tuber production. Plant height, number of leaves, and foliar characteristics were recorded approximately 4 months after planting (Table 1). 'Firecracker Red' had excellent overall plant performance ratings for the first two rating periods (Jul. 22, and Aug. 31), and a lower but good rating for Nov. 16. 'Firecracker Red' has a tendency to die back earlier in the fall than other red cultivars, but this is advantageous for the tuber production industry as there is a need to dig some cultivars for early sales. 'Firecracker Red' was the tallest cultivar evaluated in this test, out growing one of its parents, 'Red Flash' and again exhibiting a desired landscape trait.

'Firecracker Red' tubers were forced in 10-cm containers and its growth was compared to four red-fancy commercial cultivars. No. 1 tubers were planted in a peat/vermiculite mix on Jun. 24, 2002. The study was conducted in a glasshouse with 50% light exclusion during the summer in Bradenton, Fla. Average daily temperatures ranged from a low of 21° C. night to 29° C. day during the experiment. Plant height, number of leaves, and foliar characteristics were recorded 7 weeks after planting.

'Firecracker Red' had similar performance in pots compared to the other red-leaved cultivars tested or was essentially "average" with no significant differences for all measured parameters (Table 2). Thus, although 'Firecracker Red' has potential as a container plant, it appears to be better suited for use in the landscape.

In summary, 'Firecracker Red' is intended for use in the landscape or large containers. It should perform well in full sun or partial shade conditions making an ideal plant for the garden. Although extensive research and evaluations of this cultivar have been performed on small acreages, tuber producers are encouraged to plant only limited quantities of 'Firecracker Red' until they have gained experience in producing this cultivar. Standard postharvest treatment of tubers is recommended and pre-plant hot-water treatment oftubers is encouraged to prolong their life.

TABLE 1

Plant performance approximately 4 months from planting 2.54 cm tuber propagules in ground beds in full sun in 2003 and 2004. Values presented are means of three replications with three plants measured per plot per year, averaged over 2 years.

| | Plant | Leaf | | | Overall | | |
|---|---|---|---|---|---|---|---|
| | height | | length | width | performance rating[z] | | |
| Cultivar | (cm) | number | (cm) | (cm) | Early | Mid | Late |
| Cardinal | 47 | 16 | 30 | 19 | 3.7 | 4.1 | 4.3 |
| Firecracker Red | 56 | 13 | 32 | 22 | 5.0 | 4.6 | 3.8 |
| Frieda Hemple | 50 | 21 | 31 | 20 | 2.7 | 4.3 | 4.3 |
| Postman Joyner | 39 | 13 | 29 | 18 | 2.5 | 2.7 | 3.7 |
| Red Flash | 44 | 12 | 34 | 20 | 3.2 | 4.0 | 4.0 |
| LSD ($\alpha$ = 0.05) | 7.8 | 3.3 | 2.7 | 1.7 | 0.8 | 0.5 | 0.6 |

[z]Overall plant performance was rated Jul. 22 (early), Aug. 31 (mid), and Nov. 16 (late), 2004.

TABLE 2

Plant performance for *caladium* cultivars grown in 10-cm containers in a 25% shaded glasshouse, 2005, Bradenton Florida. Values represent the means of eight plants produced from intact (1) or de-eyed (D) No. 1 tubers (3.8 to 6.4 cm in diameter) planted individually per container.

| | Sprout (days)[2] | | Plant ht (cm) | | Leaf (no.) | | Leaf length (cm) | | Leaf width (cm) | |
|---|---|---|---|---|---|---|---|---|---|---|
| Cultivar | I | D | I | D | I | D | I | D | I | D |
| Firecracker Red | 17 | 19 | 37 | 42 | 9 | 16 | 22 | 22 | 17 | 15 |
| Frieda Hemple | 16 | 17 | 42 | 38 | 10 | 20 | 25 | 19 | 17 | 12 |
| Postman Joyner | 21 | 23 | 45 | 46 | 6 | 11 | 27 | 23 | 18 | 17 |
| Scarlet Beauty | 17 | 20 | 39 | 37 | 9 | 22 | 27 | 22 | 19 | 15 |
| LSD (a = 0.05) | ns | 5.2 | ns | 8.7 | ns | 5.8 | ns | 2.6 | ns | 2.0 |

[2]Number of days from planting to the first unfurled leaf

TABLE 3

*Caladium* tuber characteristics from cultivars harvested in 2003 and 2004. Values presented are means of three replications with 30 propagules per 1.2-m2 plot per year.

| | Tuber | | |
|---|---|---|---|
| | Weight (g) | P. I.[y] | Marketable (number) |
| **Year 2003** | | | |
| Cardinal | 4168 | 125 | 37 |
| Firecracker Red | 4659 | 155 | 43 |
| Frieda | 2937 | 110 | 45 |
| Postman Joyner | 3156 | 107 | 34 |
| Red Flash | 4394 | 133 | 45 |
| LSD ($\alpha$ = 0.05) | 251 | 10 | 8 |
| **Year 2004** | | | |
| Cardinal | 6161 | 168 | 41 |
| Firecracker Red | 6091 | 151 | 40 |
| Frieda Hemple | 3956 | 124 | 50 |
| Postman Joyner | 3118 | 104 | 47 |
| Red Flash | 4799 | 133 | 32 |
| LSD ($\alpha$ = 0.05) | 885 | 31 | 7.8 |

| | Tuber distribution[z] (%) | | | | |
|---|---|---|---|---|---|
| | Super mam | Mam | Jumbo | No. 1 | No. 2 |
| **Year 2003** | | | | | |
| Cardinal | 0 | 23 | 32 | 31 | 14 |
| Firecracker Red | 0 | 17 | 49 | 29 | 5 |
| Frieda Hemple | 0 | 2 | 30 | 46 | 21 |
| Postman Joyner | 1 | 6 | 48 | 32 | 11 |
| Red Flash | 0 | 16 | 29 | 28 | 27 |
| LSD ($\alpha$ = 0.05) | 2 | 12 | 37 | 30 | 14 |
| **Year 2004** | | | | | |
| Cardinal | 8 | 21 | 39 | 25 | 7 |
| Firecracker Red | 10 | 15 | 33 | 36 | 6 |
| Frieda Hemple | 0 | 4 | 27 | 51 | 19 |
| Postman Joyner | 0 | 0 | 23 | 56 | 21 |
| Red Flash | 1 | 29 | 48 | 19 | 3 |
| LSD ($\alpha$ = 0.05) | 3.2 | 16.4 | 17.0 | 28.3 | 11.3 |

[z]Tubers graded by maximum diameter; No. 2 (2.5-3.8 cm), No. 1 (3.8-6.4 cm), Jumbo (6.4-8.9 cm), Mammoth (mam = 8.9-11.4 cm), and Super Mammoth (super mam = >11.4 cm).

[y]The production index (PI) is an indicator of economic value of harvested tubers calculated as: N (No. 2s) + 2N (No. 1s) + 4N (Jumbos) + 6N (Mammoth) + 8N (Super Mammoth); where N = number of tubers in each grade.

It is claimed:

1. A new and distinct cultivar of *Caladium* plant named 'Firecracker Red', as illustrated and described.

* * * * *

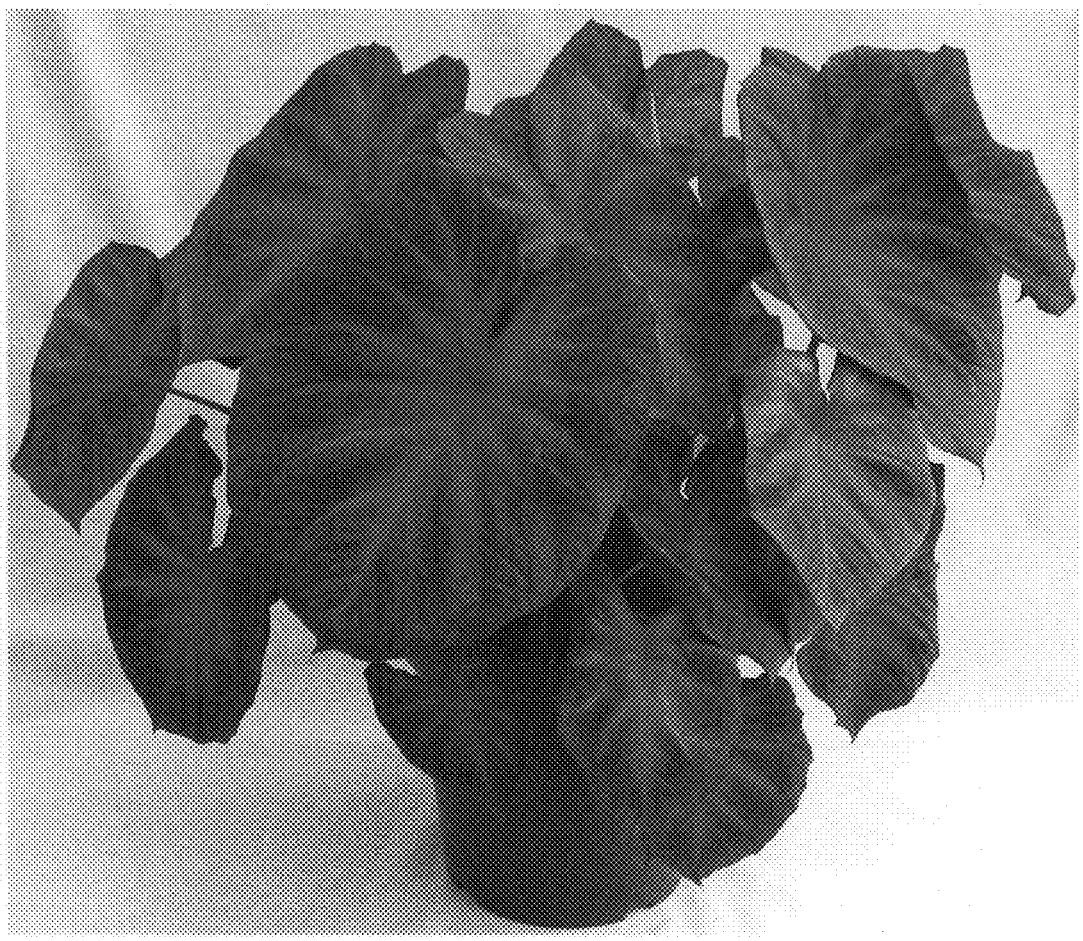
Fig. 1 – Caladium Plant named 'Firecracker Red'